United States Patent
Peters et al.

(10) Patent No.: US 7,842,093 B2
(45) Date of Patent: Nov. 30, 2010

(54) METHOD AND APPARATUS FOR A KNEE IMPLANT

(75) Inventors: Christopher Peters, Park City, UT (US); Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 178 days.

(21) Appl. No.: 11/488,851

(22) Filed: Jul. 18, 2006

(65) Prior Publication Data

US 2008/0021566 A1    Jan. 24, 2008

(51) Int. Cl.
    *A61F 2/38* (2006.01)
(52) U.S. Cl. ............... 623/20.15; 623/20.32; 623/20.35
(58) Field of Classification Search .............. 623/20.16, 623/20.28, 20.14, 19.12, 19.13, 20.35, 20.36
    See application file for complete search history.

(56) References Cited

U.S. PATENT DOCUMENTS

| | | |
|---|---|---|
| 3,534,731 A | 10/1970 | Muller |
| 3,774,244 A | 11/1973 | Walker |
| 3,868,730 A | 3/1975 | Kaufer et al. |
| RE28,841 E | 6/1976 | Allgower et al. |
| RE29,757 E | 9/1978 | Helfet |
| 4,134,158 A | 1/1979 | Laure |
| 4,167,047 A | 9/1979 | Grundei et al. |
| 4,205,400 A | 6/1980 | Shen et al. |
| 4,213,209 A | 7/1980 | Insall et al. |
| 4,219,893 A | 9/1980 | Noiles |
| 4,224,696 A | 9/1980 | Murray et al. |
| 4,224,697 A | 9/1980 | Murray et al. |
| 4,255,439 A | 3/1981 | Cooper |
| 4,301,553 A | 11/1981 | Noiles |
| 4,309,778 A | 1/1982 | Buechel et al. |
| 4,348,859 A | 9/1982 | Olsson |
| 4,404,691 A | 9/1983 | Buning et al. |
| 4,495,664 A | 1/1985 | Blanquaert |
| 4,538,305 A | 9/1985 | Engelbrecht et al. |
| 4,578,081 A | 3/1986 | Harder et al. |
| 4,624,673 A | 11/1986 | Meyer |
| 4,676,797 A | 6/1987 | Anapliotis et al. |
| 4,696,290 A | 9/1987 | Steffee |
| 4,711,639 A | 12/1987 | Grundei |
| 4,713,076 A | 12/1987 | Draenert et al. |
| 4,714,471 A | 12/1987 | Grundei |
| 4,787,907 A | 11/1988 | Carignan |
| 4,790,852 A | 12/1988 | Noiles |
| 4,790,854 A | 12/1988 | Harder et al. |
| 4,805,607 A | 2/1989 | Engelhardt et al. |
| 4,822,365 A | 4/1989 | Walker et al. |
| 4,822,366 A | 4/1989 | Bolesky |
| 4,834,758 A | 5/1989 | Lane et al. |

(Continued)

FOREIGN PATENT DOCUMENTS

DE    1575278    1/1970

(Continued)

OTHER PUBLICATIONS

Biomet Offset Tibia; Biomet Orthopedics, Inc., Dec. 2001.

(Continued)

*Primary Examiner*—David Isabella
*Assistant Examiner*—Joshua Levine
(74) *Attorney, Agent, or Firm*—Harness, Dickey

(57) ABSTRACT

A prosthesis for replacing an articulating portion of bone is provided. The prosthesis can include an adaptor operable to replace a portion of the bone. The prosthesis can further include a sleeve coupled to the adaptor. The sleeve can define an offset coupling axis. The prosthesis can also include an articulating portion operable to replace the articulating portion of the bone. The sleeve can be positionable to couple the articulating portion to the offset coupling axis at a predetermined orientation.

23 Claims, 14 Drawing Sheets

U.S. PATENT DOCUMENTS

| | | | |
|---|---|---|---|
| 4,846,839 A | 7/1989 | Noiles | |
| 4,888,021 A | 12/1989 | Forte et al. | |
| 4,904,110 A | 2/1990 | Klein | |
| 4,936,853 A | 6/1990 | Fabian et al. | |
| 4,944,757 A | 7/1990 | Martinez et al. | |
| 4,950,297 A | 8/1990 | Elloy et al. | |
| 4,950,298 A | 8/1990 | Gustilo et al. | |
| 4,959,071 A | 9/1990 | Brown et al. | |
| 4,963,155 A | 10/1990 | Lazzeri et al. | |
| 4,985,037 A | 1/1991 | Petersen | |
| 4,995,883 A | 2/1991 | Demane et al. | |
| 5,002,578 A | 3/1991 | Luman | |
| 5,002,581 A | 3/1991 | Paxson et al. | |
| 5,007,931 A | 4/1991 | Smith | |
| 5,011,496 A | 4/1991 | Forte et al. | |
| 5,019,103 A | 5/1991 | Van Zile et al. | |
| 5,057,111 A | 10/1991 | Park | |
| 5,061,271 A | 10/1991 | Van Zile | |
| 5,061,286 A | 10/1991 | Lyle | |
| 5,062,849 A | 11/1991 | Schelhas | |
| 5,071,438 A | 12/1991 | Jones et al. | |
| 5,123,928 A | 6/1992 | Moser | |
| 5,127,914 A | 7/1992 | Calderale et al. | |
| 5,133,760 A | 7/1992 | Petersen et al. | |
| 5,133,763 A | 7/1992 | Mullers et al. | |
| 5,137,535 A | 8/1992 | Keller | |
| 5,137,536 A | 8/1992 | Koshino et al. | |
| 5,139,521 A | 8/1992 | Schelhas | |
| 5,152,796 A | 10/1992 | Slamin | |
| 5,194,066 A | 3/1993 | Van Zile | |
| 5,226,915 A | 7/1993 | Bertin | |
| 5,234,431 A | 8/1993 | Keller | |
| 5,258,032 A | 11/1993 | Bertin | |
| 5,258,034 A | 11/1993 | Furlong et al. | |
| 5,269,784 A | 12/1993 | Mast | |
| 5,271,737 A | 12/1993 | Baldwin et al. | |
| 5,282,865 A | 2/1994 | Dong | |
| 5,286,253 A | 2/1994 | Fucci | |
| 5,286,260 A | 2/1994 | Bolesky et al. | |
| 5,290,288 A | 3/1994 | Vignaud et al. | |
| 5,290,313 A | 3/1994 | Heldreth | |
| 5,326,359 A | 7/1994 | Oudard et al. | |
| 5,330,534 A | 7/1994 | Herrington et al. | |
| 5,334,184 A | 8/1994 | Bimman | |
| 5,336,225 A | 8/1994 | Zang | |
| 5,342,366 A | 8/1994 | Whiteside et al. | |
| 5,352,227 A | 10/1994 | O'Hara | |
| 5,358,526 A | 10/1994 | Tornier et al. | |
| 5,370,701 A | 12/1994 | Finn | |
| 5,387,240 A | 2/1995 | Pottenger et al. | |
| 5,387,241 A | 2/1995 | Hayes | |
| 5,397,360 A | 3/1995 | Cohen et al. | |
| 5,405,395 A | 4/1995 | Coates | |
| 5,405,396 A | 4/1995 | Heldreth et al. | |
| 5,413,605 A | 5/1995 | Ashby et al. | |
| 5,545,228 A | 8/1996 | Kambin | |
| 5,556,433 A | 9/1996 | Gabriel et al. | |
| 5,557,433 A | 9/1996 | Maruyama et al. | |
| 5,593,449 A | 1/1997 | Roberson, Jr. | |
| 5,609,641 A | 3/1997 | Johnson et al. | |
| 5,609,642 A | 3/1997 | Johnson et al. | |
| 5,613,970 A | 3/1997 | Houston et al. | |
| 5,620,445 A | 4/1997 | Brosnahan et al. | |
| 5,634,927 A | 6/1997 | Houston et al. | |
| 5,643,303 A | 7/1997 | Donahue | |
| 5,645,607 A | 7/1997 | Hickey | |
| 5,658,349 A | 8/1997 | Brooks et al. | |
| 5,683,469 A | 11/1997 | Johnson et al. | |
| 5,683,470 A | 11/1997 | Johnson et al. | |
| 5,702,460 A | 12/1997 | Carls et al. | |
| 5,766,255 A | 6/1998 | Slamin et al. | |
| 5,776,200 A | 7/1998 | Johnson et al. | |
| 5,782,920 A | 7/1998 | Colleran | |
| 5,782,921 A | 7/1998 | Colleran et al. | |
| 5,800,552 A * | 9/1998 | Forte | 623/20.27 |
| 5,824,097 A | 10/1998 | Gabriel et al. | |
| 5,824,104 A | 10/1998 | Tuke | |
| 5,879,391 A | 3/1999 | Slamin | |
| 5,902,340 A | 5/1999 | White et al. | |
| 5,944,756 A | 8/1999 | Fischetti et al. | |
| 6,039,764 A | 3/2000 | Pottenger et al. | |
| 6,063,091 A | 5/2000 | Lombardo et al. | |
| 6,063,122 A | 5/2000 | O'Neil et al. | |
| 6,071,311 A | 6/2000 | O'Neil et al. | |
| 6,102,956 A | 8/2000 | Kranz | |
| 6,126,693 A | 10/2000 | O'Neil et al. | |
| 6,139,584 A | 10/2000 | Ochoa et al. | |
| 6,146,424 A | 11/2000 | Gray, Jr. et al. | |
| 6,149,687 A | 11/2000 | Gray, Jr. et al. | |
| 6,162,255 A | 12/2000 | Oyola | |
| 6,171,342 B1 | 1/2001 | O'Neil et al. | |
| 6,214,052 B1 | 4/2001 | Burkinshaw | |
| 6,217,619 B1 | 4/2001 | Keller et al. | |
| 6,228,091 B1 | 5/2001 | Lombardo et al. | |
| 6,228,120 B1 | 5/2001 | Leonard et al. | |
| 6,264,699 B1 | 7/2001 | Noiles et al. | |
| 6,306,172 B1 | 10/2001 | O'Neil et al. | |
| 6,423,096 B1 | 7/2002 | Musset et al. | |
| 6,447,549 B1 | 9/2002 | Taft | |
| 6,505,387 B1 | 1/2003 | Yatskov et al. | |
| 6,506,216 B1 * | 1/2003 | McCue et al. | 623/20.34 |
| 6,613,092 B1 | 9/2003 | Kana et al. | |
| 6,663,670 B2 * | 12/2003 | Rogers et al. | 623/23.47 |
| 6,673,114 B2 | 1/2004 | Hartdegen et al. | |
| 6,706,072 B2 | 3/2004 | Dwyer et al. | |
| 6,736,852 B2 * | 5/2004 | Callaway et al. | 623/19.14 |
| 6,749,637 B1 | 6/2004 | Bahler | |
| 6,783,551 B1 | 8/2004 | Metzger et al. | |
| 6,797,006 B2 * | 9/2004 | Hodorek | 623/20.36 |
| 6,923,832 B1 | 8/2005 | Sharkey et al. | |
| 6,953,479 B2 | 10/2005 | Carson et al. | |
| 6,972,039 B2 | 12/2005 | Metzger et al. | |
| 6,986,791 B1 | 1/2006 | Metzger | |
| 7,153,326 B1 | 12/2006 | Metzger | |
| 7,468,078 B2 * | 12/2008 | Sederholm et al. | 623/22.42 |
| 2003/0014120 A1 | 1/2003 | Carson et al. | |
| 2003/0055508 A1 | 3/2003 | Metzger et al. | |
| 2003/0065397 A1 | 4/2003 | Hanssen et al. | |
| 2003/0180117 A1 | 9/2003 | Niku | |
| 2003/0204263 A1 | 10/2003 | Justin et al. | |
| 2004/0049284 A1 * | 3/2004 | German et al. | 623/20.15 |
| 2004/0162619 A1 | 8/2004 | Blaylock et al. | |
| 2004/0172137 A1 | 9/2004 | Blaylock et al. | |
| 2004/0199260 A1 * | 10/2004 | Pope et al. | 623/23.5 |
| 2005/0154470 A1 | 7/2005 | Sekel | |

FOREIGN PATENT DOCUMENTS

| | | |
|---|---|---|
| EP | 010527 | 4/1980 |
| EP | 0144667 | 6/1985 |
| EP | 0307655 | 3/1989 |
| EP | 0495340 | 7/1992 |
| EP | 0529408 | 3/1993 |
| EP | 0531263 | 3/1993 |
| EP | 0621019 | 10/1994 |
| FR | 2288509 | 5/1976 |
| FR | 2701387 | 8/1994 |
| GB | 2259253 | 3/1993 |
| GB | 2312168 | 10/1997 |

| | | |
|---|---|---|
| WO | WO-9709939 | 3/1997 |

OTHER PUBLICATIONS

International Search Report for PCT/US2007/016148 mailed Nov. 27, 2007, claiming priority to U.S. Appl. No. 11/488,851, filed Jul. 18, 2006.

International Preliminary Report on Patentability for PCT/US2007/016148 mailed Jan. 29, 2009, claiming priority to U.S. Appl. No. 11/488,851, filed Jul. 18, 2006.

Written Opinion for PCT/US2007/016148 mailed Nov. 27, 2007, claiming priority to U.S. Appl. No. 11/488,851, filed Jul. 18, 2006.

* cited by examiner

METHOD AND APPARATUS FOR A KNEE IMPLANT

FIELD

The present disclosure relates generally to implants, and particularly to a method and apparatus for a knee implant.

BACKGROUND

The statements in this section merely provide background information related to the present disclosure and may not constitute prior art.

Many portions of the human anatomy naturally articulate relative to one another. Generally, the articulation between the portions of the anatomy is substantially smooth and without abrasion. This articulation is allowed by the presence of natural tissues, such as cartilage and strong bone.

Over time, however, due to injury, stress, degenerative health issues and various other issues, articulation of the various portions of the anatomy can become rough or impractical. For example, injury can cause the cartilage or the boney structure to become weak, damaged, or non-existent. Therefore, the articulation of the anatomical portions is no longer possible for the individual.

At such times, it can be desirable to replace the anatomical portions with a prosthetic portion such that normal or easy articulation can be reproduced. A distal end of a femur naturally articulates with respect to a tibia to form a knee joint. After injury or other degenerative processes, the distal end of the femur and the tibia and can become rough or damaged. Therefore, it can be desirable to replace the distal end of the femur and the tibia with a prosthesis.

SUMMARY

A prosthesis for replacing an articulating portion of bone. The prosthesis can include an adaptor operable to replace a portion of the bone. The prosthesis can further include a sleeve coupled to the adaptor. The sleeve can define an offset coupling axis. The prosthesis can also include an articulating portion operable to replace the articulating portion of the bone. The sleeve can be positionable to couple the articulating portion relative to the offset coupling axis at a predetermined orientation.

Provided is a prosthesis for replacing an articulating portion of bone. The prosthesis can include an adaptor operable to replace a portion of the bone. The adaptor can define an offset coupling axis. The prosthesis can also include an articulating portion operable to replace the articulating portion of the bone. The articulating portion can be adapted to be coupled to the offset coupling axis. The adaptor can be composed of a porous metal material.

A prosthesis for replacing an articulating portion of bone is further provided. The prosthesis can include an adaptor operable to replace a portion of the bone. The adaptor can include a surface, an apex and at least one sidewall. The sidewall can couple the surface to the apex. The prosthesis can further include an articulating portion operable to replace the articulating portion of the bone. The articulating portion can be adapted to be coupled to the adaptor. The prosthesis can also include at least one augment coupled to at least a portion of the sidewall of the adaptor. The adaptor and the augment can be composed of a porous metal material.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
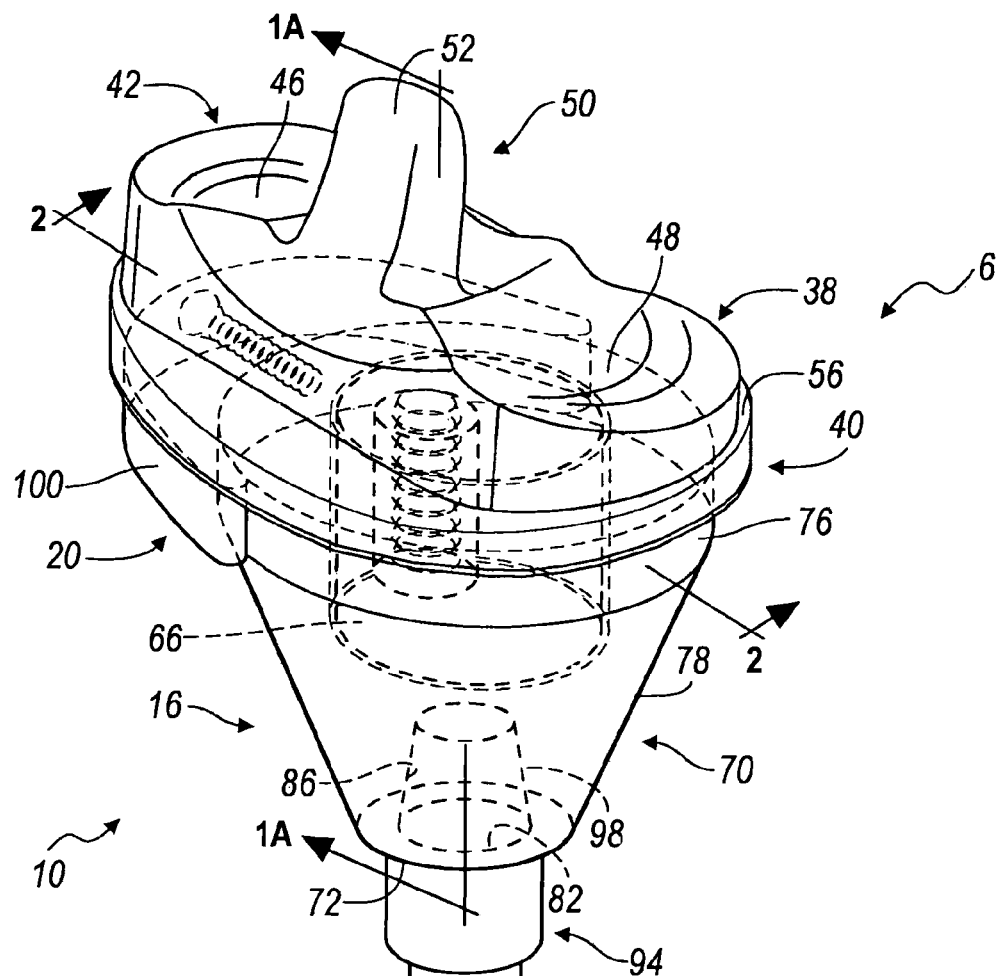
FIG. 1 is a perspective view of a knee implant according to the present disclosure.
Figure 1:
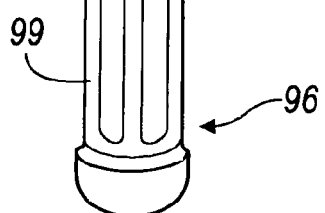

The following description is merely exemplary in nature and is not intended to limit the present disclosure, application, or uses. It should be understood that throughout the drawings, corresponding reference numerals indicate like or corresponding parts and features. Although the following description is related generally to a prosthesis that can be positioned in a prepared portion of the anatomy, such as in a tibia or a femur, it will be understood that the prosthesis, as described and claimed herein, can be used with any appropriate surgical procedure. In addition, it should be noted that the knee implant of the present disclosure can be used in a revision knee implant procedure. Therefore, it will be understood that the following discussions are not intended to limit the scope of the appended claims.

Figure 1A:
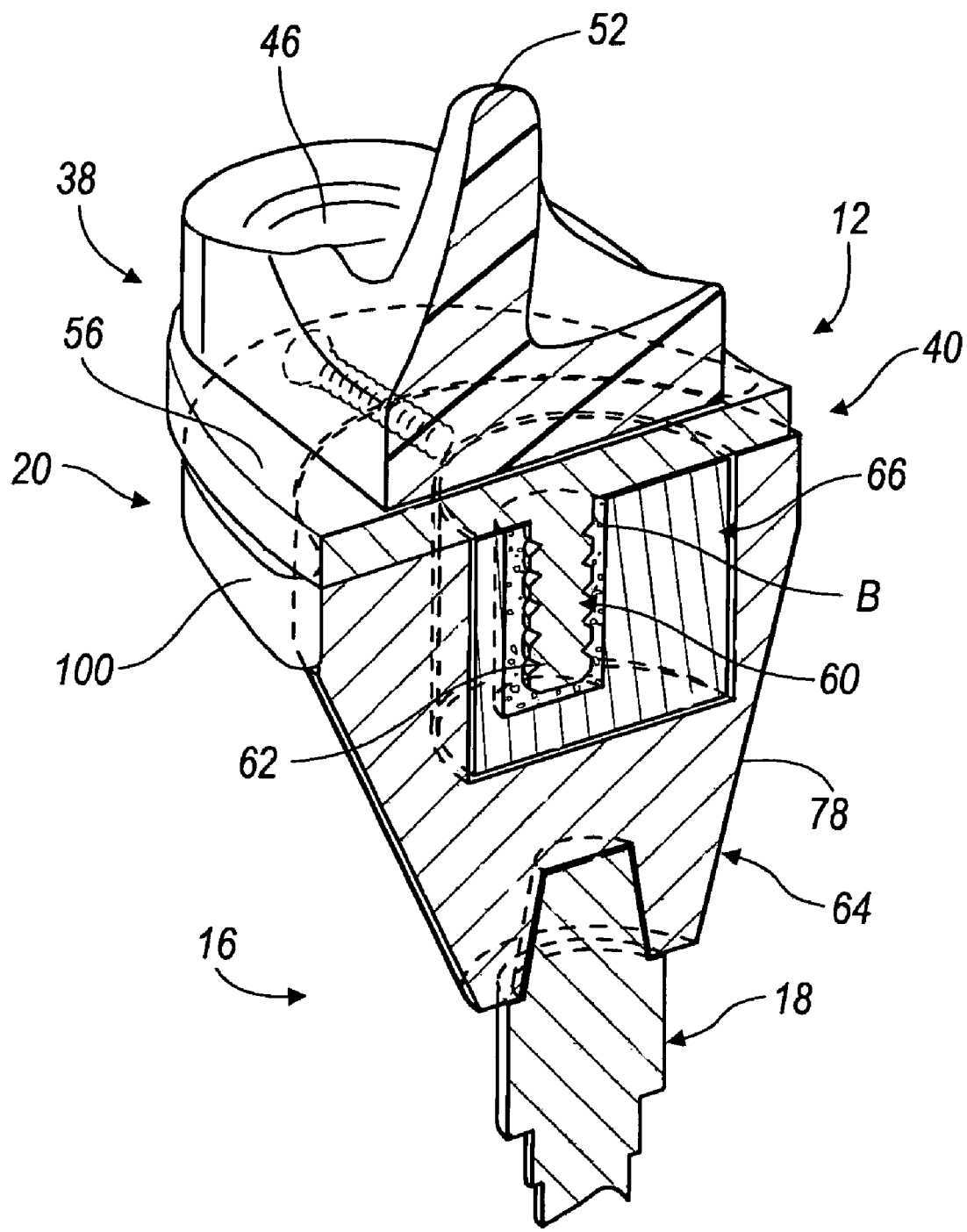
FIG. 1A is a cross-sectional view of the knee implant of FIG. 1, taken along line 1A-1A of FIG. 1.
Figure 2:
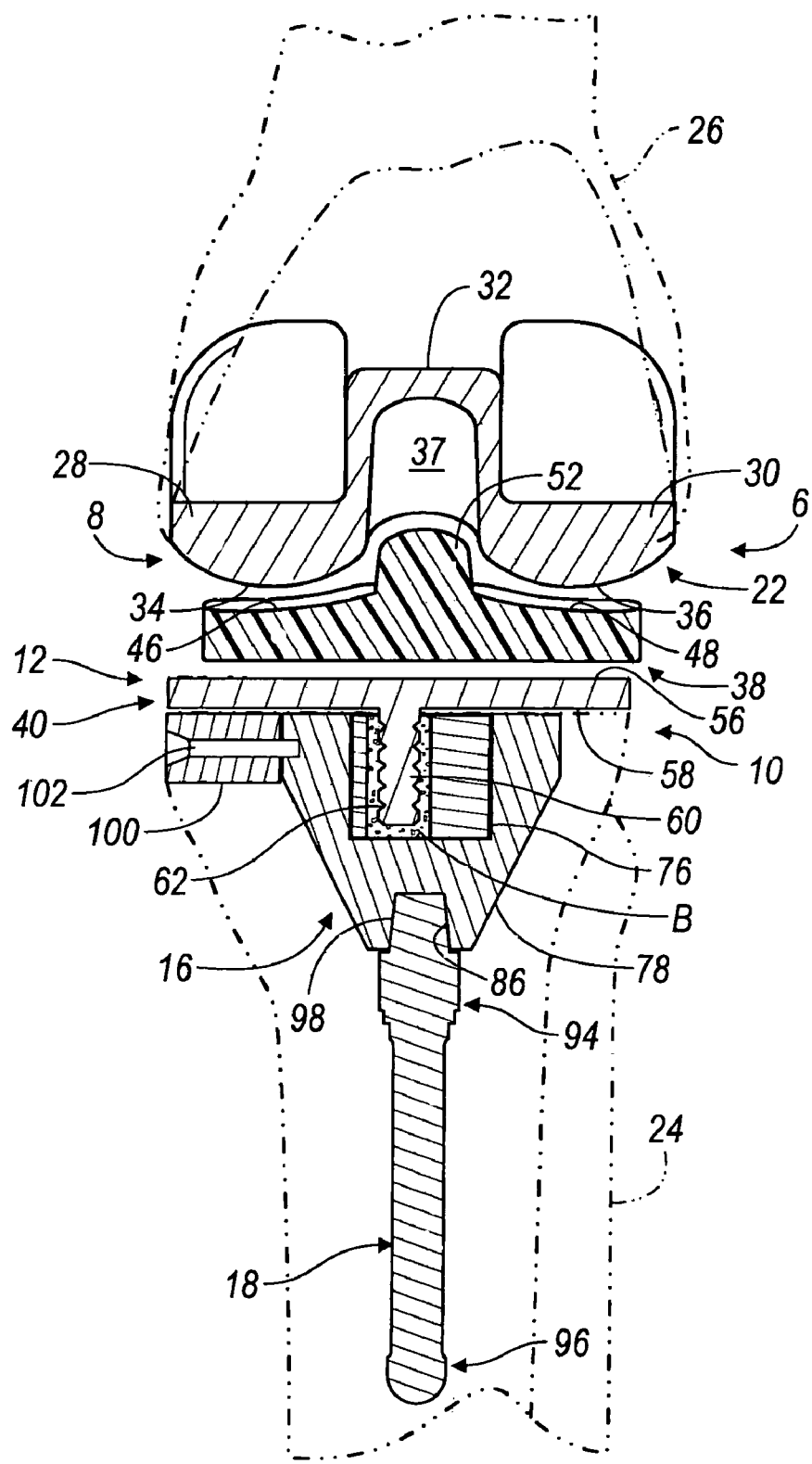
FIG. 2 is a cross-sectional view of the knee implant of FIG. 1 taken along line 2-2 of FIG. 1, illustrating the knee implant of FIG. 1 engaged with a selected portion of the anatomy.

As will be discussed in more detail herein, a knee implant assembly 6 is taught. With reference to FIGS. 1, 1A and 2, the knee implant assembly 6 can include a femoral component 8 and a tibial component 10, each of which can include an articulating portion. In one exemplary teaching, the tibial component 10 can include an articulating or mating portion 12 and an adaptor assembly 16. It should be noted that as the knee implant assembly 6 can be used with any suitable knee prosthesis, such as a cruciate retaining knee prosthesis, for example, the AGC® Total Knee System™, a posterior stabilized knee prosthesis, for example, the AGC® Tradition High-Post Knee System™, or a hinged knee prosthesis, for example, the Orthopaedic Salvage System™, all provided by Biomet, Inc. of Warsaw, Ind., the mating portion 12 and femoral component 8 can be configured as needed for the particular surgical application. The tibial component 10 can also include a stem 18 and an augment system 20 both of which can be coupled to the adaptor assembly 16. The mating portion 12 of the tibial component 10 can enable the femoral component 8 to articulate with respect to the tibial component 10.

With particular reference to FIG. 2, the femoral component 8 can be any generally known suitable femoral component 8, and thus, the femoral component 8 need not be discussed in great detail herein. Briefly, however, the femoral component 8 can include an articulating portion or body 22. The body 22 can be adapted to secure to a distal end of a femur 26 to enable the femur 26 to articulate with the tibial component 10. The body 22 can include a first condylar portion 28, a second condylar portion 30 and an intercondylar portion 32. The first condylar portion 28 can define a first femoral bearing surface 34, while the second condylar portion 30 can define a second femoral bearing surface 36. The intercondylar portion 32 can couple the first condylar portion 28 to the second condylar portion 30 and can define an intercondylar recess 37. The intercondylar recess 37 can rotatably couple the body 22 to the mating portion 12 of the tibial component 10, and can define an throughbore 35 (FIG. 2B) as will be discussed in greater detail below. Further detail regarding the femoral component 8 is outside the scope of the present disclosure but an exemplary femoral component 8 is disclosed in greater detail in commonly assigned United States patent entitled "Floating Bearing Knee Joint Prosthesis With A Fixed Tibial Post," filed on Dec. 6, 2005, U.S. Pat. No. 6,972,039, which is incorporated by reference herein in its entirety.

Figure 3:
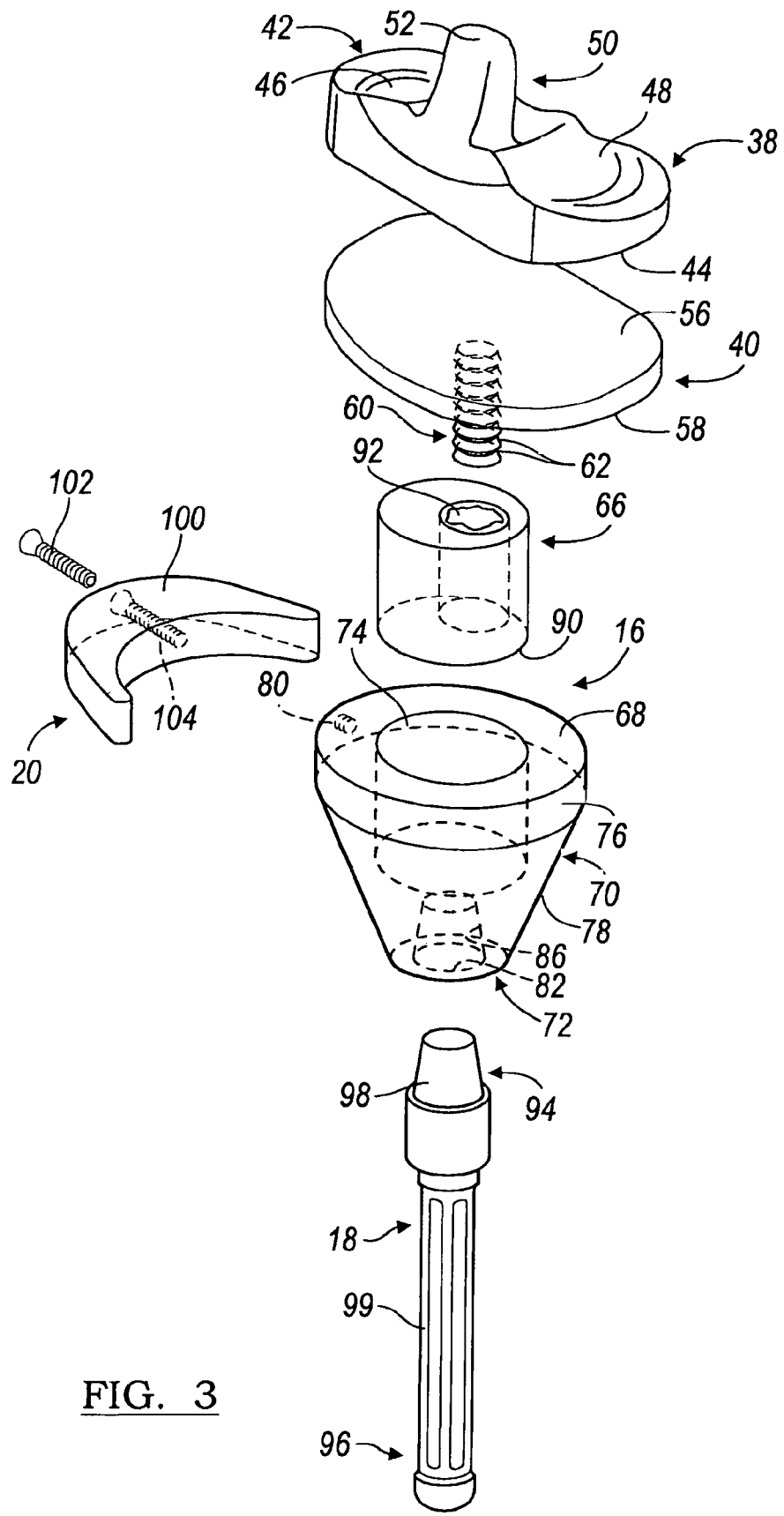
FIG. 3 is an exploded view of the knee implant of FIG. 1.

With continuing reference to FIG. 2, and with additional reference to FIGS. 1-3, the mating portion 12 can include a bearing member 38 and a tray 40. The bearing member 38 can include a first bearing surface 42 and a second bearing surface 44. The first bearing surface 42 can generally include a first bearing portion 46, a second bearing portion 48 and an intermediate portion 50 to enable the femoral component 8 to articulate with the bearing member 38. Generally, the first bearing portion 46 can be configured to engage and articulate with the first femoral bearing surface 34 of the first condylar portion 28 and second bearing portion 48 can be configured to engage and articulate with the second femoral bearing surface 36 of the second condylar portion 30, as is generally known and discussed in greater detail herein.

Figures 2A, 2B:
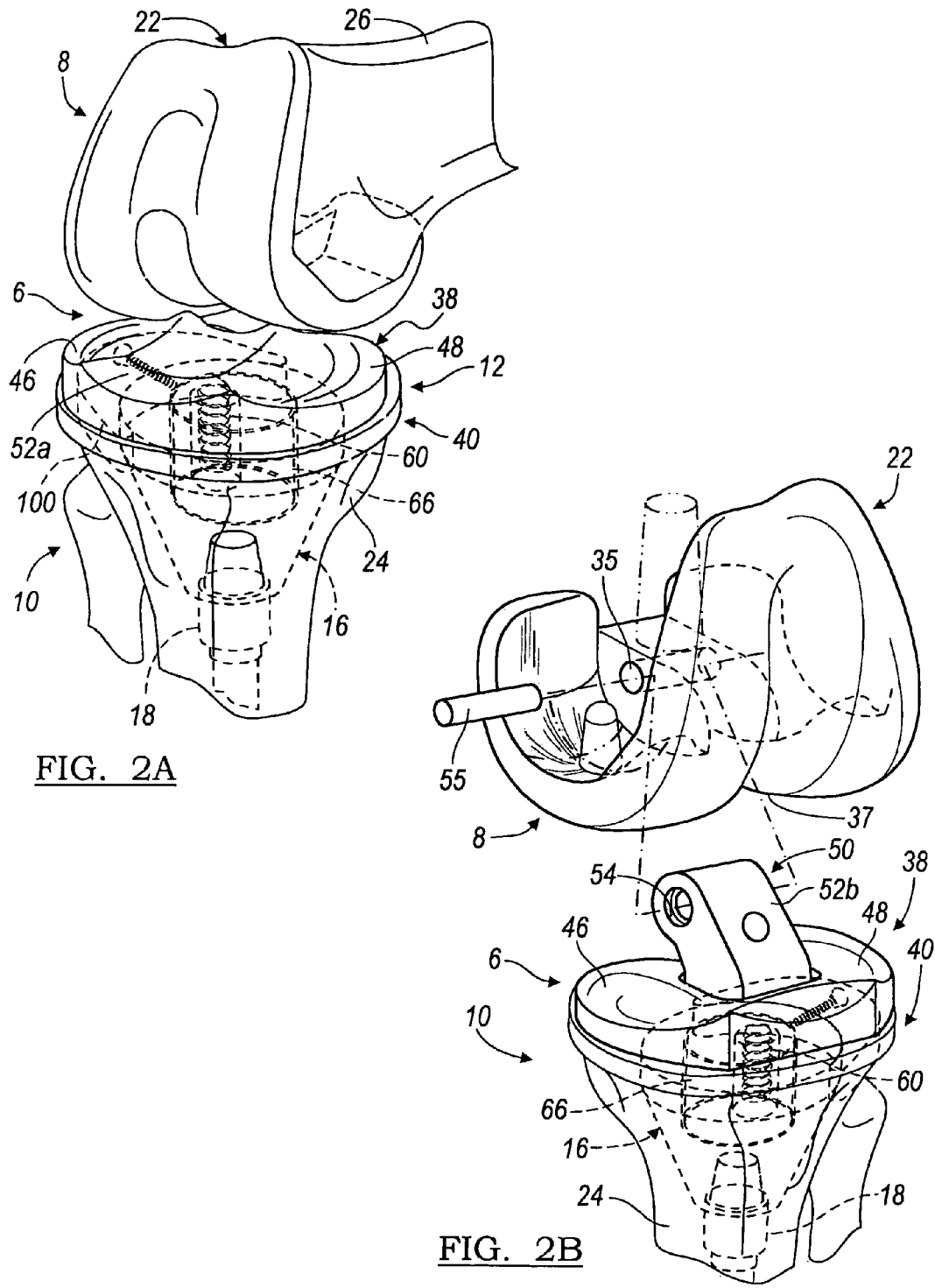
FIG. 2A is a perspective view of a first alternative knee implant according to the present disclosure.
FIG. 2B is a perspective view of a second alternative knee implant according to the present disclosure.

The intermediate portion 50 can be positioned between the first bearing portion 46 and the second bearing portion 48. The intermediate portion 50 can interface with the intercondylar recess 37 of the femoral component 8. The intermediate portion 50 can comprise a guide post 52, as in the case of posterior stabilized knee prosthesis (FIG. 2), or can be a slightly raised protrusion 52a, as in the case of a cruciate retaining knee prosthesis (FIG. 2A). Alternatively, the intermediate portion 50 can comprise a guide post 52b with a throughbore 54 for receipt of a pin 55 (FIG. 2B) to couple the bearing portion 38 to the femoral component 8, through the throughbore 35 as in the case of a hinged knee prosthesis.

The bearing member 38 can be formed of any suitable material, such as a surgical grade, low friction, low wearing polymeric material, for example, ultra-high molecular weight polyethylene (UHMWPE). Further detail regarding the bearing member 38 is outside the scope of the present disclosure but an exemplary bearing member 38 is disclosed in greater detail in commonly assigned United States patent entitled "Floating Bearing Knee Joint Prosthesis With A Fixed Tibial Post," filed on Dec. 6, 2005, U.S. Pat. No. 6,972,039, previously incorporated by reference herein. The second bearing surface 44 of the bearing member 38 can be generally smooth and planar. The second bearing surface 44 can be coupled to, rotatable about the tray 40, or can slideably engage the tray 40, as is generally known in the art.

The tray 40 can include a first surface 56, a second surface 58 and a mating portion or projection 60. The tray 40 can be composed of a biocompatible metal or metal alloy, such as cobalt-chromium-molybdenum, titanium, or titanium alloy. The first surface 56 can be configured to mate with the second bearing surface 44 of the bearing member 38 and can be generally planar. The first surface 56 can have a high polish to slideably engage the second bearing surface 44 of the bearing member 38. It should be understood, however, that the tray 40 could engage the bearing member 38 through any appropriate fashion, and could alternatively be coupled to the bearing member 38 similar to the AGC® Total Knee System™, provided by Biomet, Inc. of Warsaw, Ind. The second surface 58 of the tray 40 can be configured to mate with the adaptor assembly 16 and can also be generally planar. The second surface 58 can be coupled to or can define the mating projection 60.

Generally, the mating projection 60 can be integrally formed with the tray 40, however, the mating projection 60 could be coupled to the tray 40 through any appropriate technique, such as the use of bio-compatible mechanical fasteners and/or adhesive. The mating projection 60 can generally be configured to mate with the adaptor assembly 16, and can include at least one or a plurality of grooves 62. The grooves 62 can provide channels for receipt of a bio-compatible adhesive to couple the tray 40 to the adaptor assembly 16, as will be discussed in greater detail herein. It will be understood that although the mating projection 60 is shown as cylindrical, the mating projection 60 could be any desired shape, such as starred, rectangular, square, oval, or any other polygonal shape, and alternatively, the mating projection 60 could be keyed to mate with the adaptor assembly 16. Alternatively, it should be noted that the tray 40 could define an aperture (not shown) for receipt of a mechanical fastener, such as a bolt, screw or the like, to couple the tray 40 to the adaptor assembly 16.

Figure 3A:
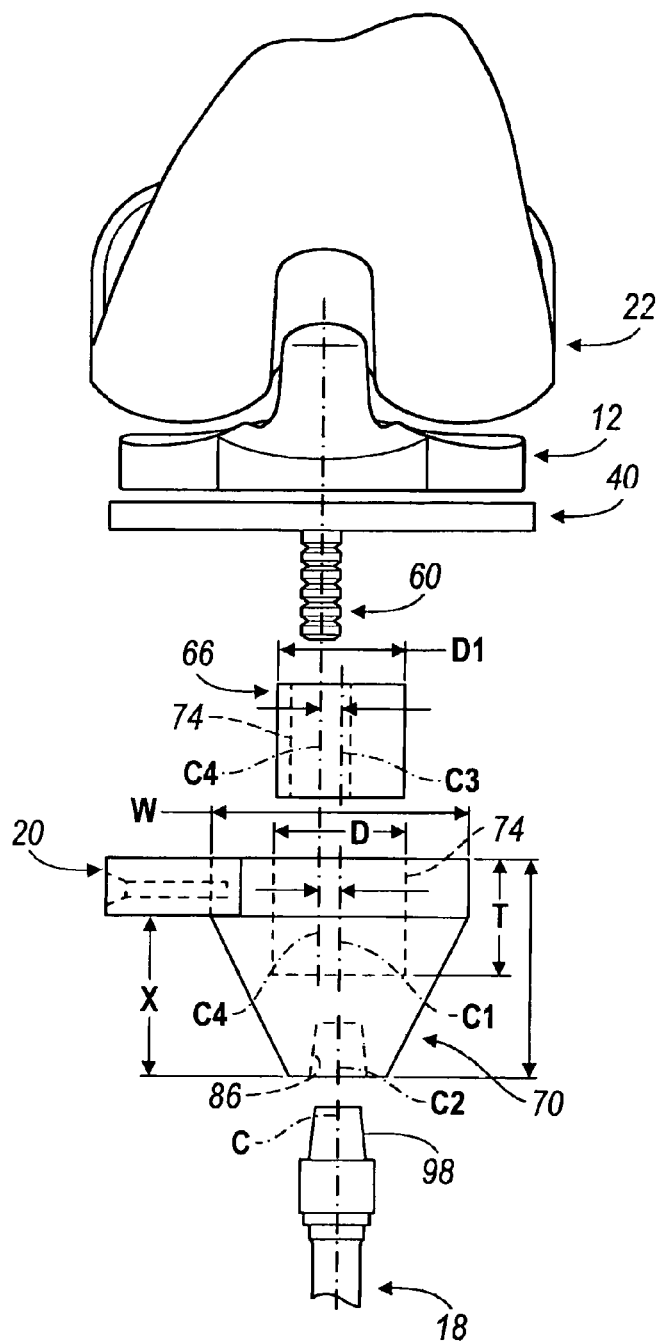
FIG. 3A is a front view of the knee implant of FIG. 3.

The adaptor assembly 16 can include an adaptor 64 and a sleeve 66. The sleeve 66 can be configured to receive the mating projection 60 of the tray 40 to couple the tray 40 to the adaptor assembly 16, as will be discussed in greater detail herein. The adaptor 64 can include a first portion or surface 68, sidewalls or a base portion 70 and an apex or second surface 72. With continuing reference to FIGS. 1-3, and with additional reference to FIG. 3A, the adaptor 64 can be generally conical in shape and symmetric about a centerline C, however, any suitable shape, such as cylindrical, could be employed. The adaptor 64 can be composed of a porous metal material, but any other suitable bio-compatible material, such as titanium, could be employed. Exemplary porous metal materials and exemplary methods for making porous metal may be found in co-pending applications, U.S. Ser. No. (11/

357,929, filed Feb. 17, 2006), entitled "Method and Apparatus for Forming Porous Metal Implants", and U.S. Ser. Nos. (11/111,123 filed, Apr. 21, 2005; Ser. No. 11/294,692, filed Dec. 5, 2005; and Ser. No. 11/357,868, filed Feb. 17, 2006), each entitled "Method and Apparatus for use of Porous Implants," all assigned to Biomet Manufacturing Corp. of Warsaw Ind., and incorporated herein by reference in their entirety.

The first surface 68 of the adaptor 64 can be configured to mate with the second surface 58 of the tray 40, and can be generally planar. The first surface 68 can define a bore 74 for receipt of the sleeve 66. It should be noted that although the bore 74 is shown as cylindrical, the bore 74 can have any desired shape, such as starred, rectangular, square, or any other polygonal shape, and alternatively could be keyed to mate with the sleeve 66. The bore 74 can have a diameter D and a depth T. The bore 74 can have a centerline C1 which can be concentric to the centerline C of the adaptor 64. The diameter D of the bore 74 can generally be slightly larger than a diameter D1 of the sleeve 66 so that the sleeve 66 can be slideably coupled to the bore 74, as will be discussed in greater detail herein. Generally, the first surface 68 can be integrally formed with the base portion 70; however, the first surface 68 and base portion 70 could also be coupled together via bio-compatible mechanical fasteners and/or adhesives.

The base portion 70 can be configured to mate with a portion of the anatomy, such as the tibia 24. Generally, the base portion 70 can define a base 76 and tapered sidewalls 78 which can extend from the base 76 for a selected distance X into the tibia 24. It will be understood that the taper on the sidewalls 78 and the distance X to which the sidewalls 78 extend can be selected based on the particular application, such that a variety of configurations of the sidewalls 78 can be employed with a variety of different tibias 24. Further, a width W of the base 76 can be varied as necessary to correspond to the particular anatomy. The base 76 can include at least one or a plurality of apertures 80 to couple the augment system 20 to the adaptor 64, as will be discussed in greater detail herein. The sidewalls 78 can generally taper to the second surface 72.

The second surface 72 of the adaptor 64 can be generally planar, and can be configured to mate with a portion of the anatomy, such as the tibia 24. The second surface 72 can define a bore 82. It should be noted that although the second surface 72 is shown as forming a platform 84 about the bore 82, the second surface 72 could alternatively comprise an apex defining just the bore 82. Generally, a centerline C2 of the bore 82 can be concentric to the centerline C of the adaptor 64. The bore 82 can define a tapered surface 86, which can be configured to couple the stem 18 to the adaptor 64, through a frictional lock, such as a Morse taper, as will be discussed herein. It should be noted, however, that any suitable technique could be used to couple the stem 18 to the adaptor 64, such as bio-compatible mechanical fasteners and/or adhesives. In addition, as will be discussed herein, the bore 82 can generally be configured to receive any type of stem 18 employed to couple the adaptor assembly 16 to the portion of the anatomy, such as the tibia 24.

The sleeve 66 can be slideably and rotatably received in the bore 74 of the first surface 68 of the adaptor 64. The sleeve 66 can be coupled to the bore 74 through any appropriate technique, such as a slip fit, taper fit or press fit, so long as the sleeve 66 is positionable within the bore 74. Generally the sleeve 66 can be cylindrical, and can have a centerline C3 which can be concentric to the centerline C of the adaptor 64. It should be noted that although the sleeve 66 is shown as cylindrical, the sleeve 66 could have any desired shape, such as such as oval, starred, rectangular, square, or any other polygonal shape, and alternatively, the sleeve 66 could be keyed to mate with the bore 74 of the adaptor 64. The sleeve 66 can be composed of a bio-compatible metal or metal alloy, such as titanium, titanium alloy, cobalt-chromium-molybdenum or the like.

The sleeve 66 can include a first surface 88 and a second surface 90. The first surface 88 can define an offset coupling axis, which can include a bore 92. The bore 92 can be cylindrical and can have a centerline C4 which can be offset from the centerline C of the adaptor 64. The bore 92 can be configured to receive the mating projection 60 of the tray 40, to couple the tray 40 to the adaptor assembly 16. It will be understood that although the bore 92 is shown as cylindrical, the bore 92 could be any desired shape, such as starred, rectangular, square, oval, or any other polygonal shape, and alternatively, could be keyed to mate with the mating projection 60 of the tray 40.

The bore 92 can be sized larger than the mating projection 60 to enable the receipt of a bio-compatible adhesive material, such as a bio-compatible cement B. The biocompatible adhesive material can be received into the bore 92 with the mating projection 60 disposed within the bore 92 to affix the tray 40 to the adaptor assembly 16. Alternatively, the bore 92 could be threaded for receipt of a mechanical fastener, such as a screw or bolt, to couple the tray 40 to the sleeve 66 (not shown). It should also be noted that the sleeve 66 as described herein is optional and the tray 40 could be coupled to an offset coupling axis defined in the bore 74 of the adaptor 64 (not shown). The adaptor assembly 16 can be coupled to the stem 18 and the augment system 20.

The stem 18 can include a first end 94 and a second end 96. The first end 94 of the stem 18 can be coupled to the adaptor assembly 16 and the second end 96 can be coupled to a portion of the anatomy, such as the tibia 24. The stem 18 can be composed of any suitable bio-compatible material, such as a bio-compatible metal or metal alloy. It should be understood, however, that the stem 18 as described herein, is merely exemplary, as various stems could be employed with the adaptor assembly 16 as is generally known in the art.

The first end 94 of the stem 18 can generally include a tapered surface 98 configured to engage the tapered surface 86 of the bore 82 of the adaptor 64 to couple the stem 18 to the adaptor 64. The tapered surface 86 can generally frictionally lock the stem 18 to the adaptor 64, and can comprise a Morse taper, however any other technique could be used to couple the stem 18 to the adaptor 64, such as mechanical fasteners and/or adhesives. The first end 94 can be coupled to the second end 96, and could also be integrally formed with the second end 96. The second end 96 of the stem 18 could have any suitable configuration as necessary to mate with the anatomy, and further, the second end 96 of the stem 18 can be offset from the first end 94 of the stem 18 if desired (not shown). The second end 96 of the stem 18 can include ribs 99 to facilitate the engagement of the stem 18 with the anatomy. It will be understood, however, that the ribs 99 are optional.

The augment system 20 can be coupled to the base 76 of the base portion 70 of the adaptor 64. It should be noted that the augment system 20, as disclosed herein, can be used with any suitable knee implant assembly and further the knee implant assembly 6 can be implemented without the augment system 20 if desired. Generally, the augment system 20 can include at least one or a plurality of augments 100 which can be mechanically fastened to at least a portion of the sidewalls or base portion 70 of the adaptor 64 via at least one or a plurality of bio-compatible fasteners 102. It should be understood, however, that the augment 100 could be coupled to the base portion 70 of the adaptor 64 through any other suitable technique, such as the use of a bio-compatible adhesive or the like.

The augment 100 can be composed of a suitable bio-compatible material, such as a metal or metal alloy, and can be composed of a porous metal material, previously incorporated by reference herein. The augment 100 can be any shape required for the particular portion of the anatomy, such as semi-circular, rectangular or the like. If a fastener 102 is employed to couple the augment 100 to the anatomy, then the augment 100 can define at least one throughbore 104 for receipt of the fastener 102.

Figure 4:
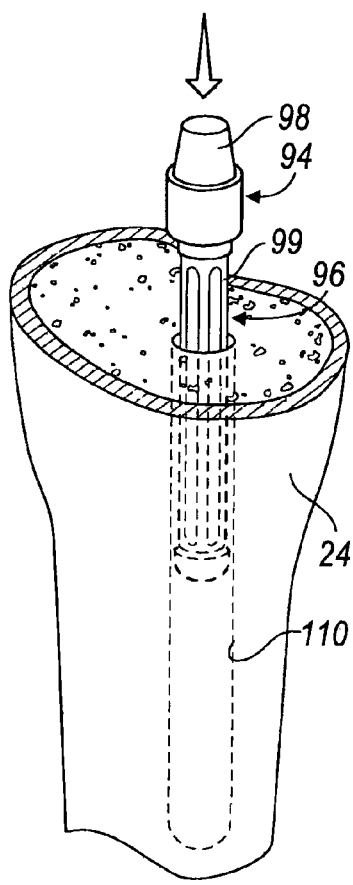
FIG. 4 is an environmental view of a first procedure for coupling the knee implant to the selected portion of the anatomy.
Figure 5:
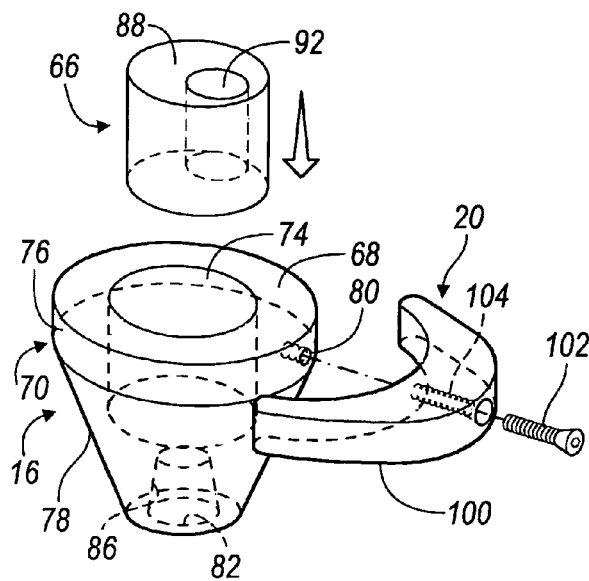
FIG. 5 is an environmental view of a second procedure for coupling the knee implant to the selected portion of the anatomy.

With additional reference now to FIG. 4, in order to couple the knee implant assembly 6 to the anatomy, the tibia 24 and femur 26 (not shown) can be resected and prepared as is generally known in the art. Then, the femoral component 8 can be coupled to the femur 26, as is generally known in the art. Then, the adaptor 64 can be coupled to the stem 18 and then the stem 18 can be press-fitted into a first bore 110 formed in the tibia 24. With additional reference to FIG. 5, if the augment system 20 is employed, the augment system 20 can be coupled to the adaptor 64 prior to the adaptor 64 being coupled to the stem 18.

Figure 6:
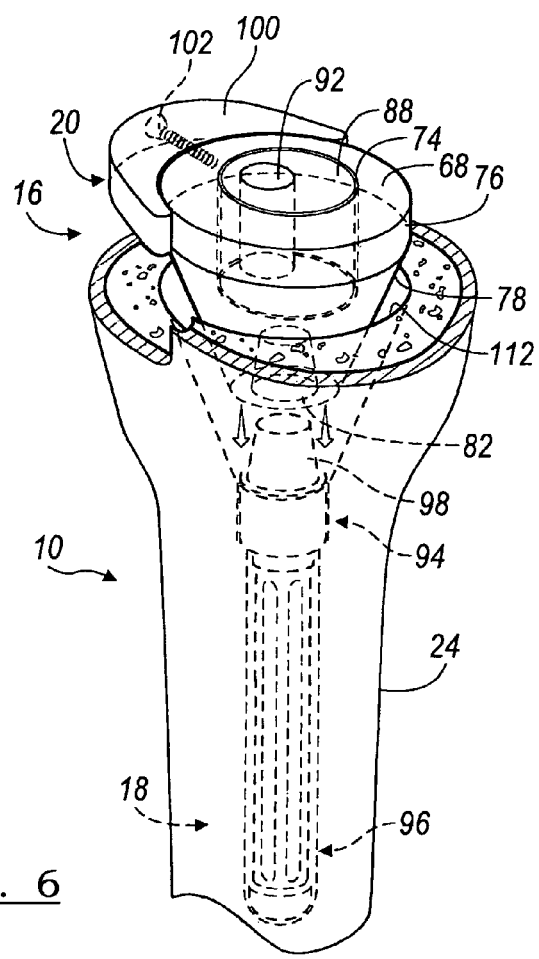
FIG. 6 is an environmental view of a third procedure for coupling the knee implant to the selected portion of the anatomy.

In order to couple the augment 100 to the adaptor 64, the base 76 of the adaptor 64 can be drilled (not shown) to form the aperture 80. Then, the fastener 102 can be inserted through the throughbore 104 of the augment 100 and into the aperture 80 of the adaptor 64 to couple the augment 100 to the adaptor 64. After the desired number of augments 100 are coupled to the base 76 of the adaptor 64, the sleeve 66 with the most appropriate offset can be selected and the sleeve 66 can then be coupled to the adaptor 64. With additional reference to FIG. 6, the adaptor assembly 16 can then be coupled to the stem 18, such that the tapered surface 86 of the bore 82 of the adaptor 64 can engage the tapered surface 98 of the first end 94 of the stem 18 to couple the stem 18 to the adaptor 64.

Figure 7:
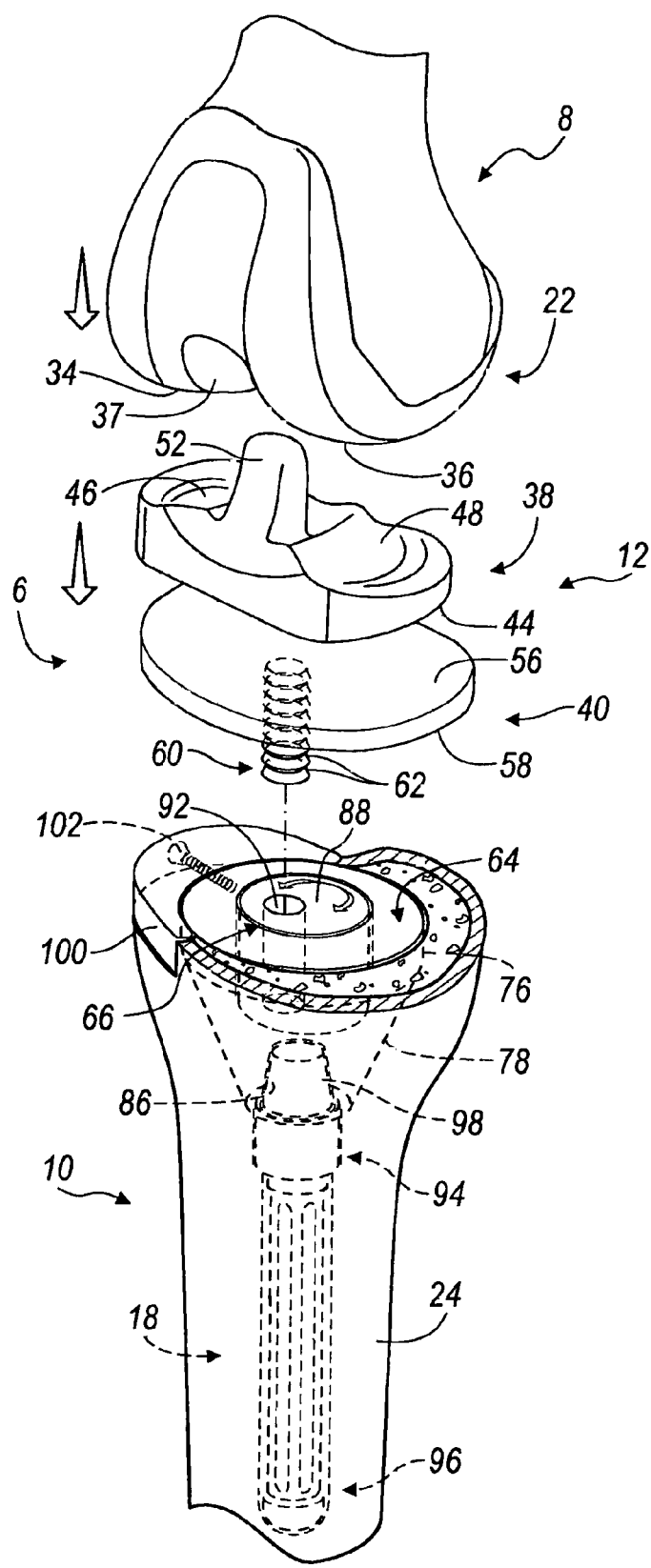
FIG. 7 is an environmental view of a fourth procedure for coupling the knee implant to the selected portion of the anatomy.

After the adaptor assembly 16 is coupled to the stem 18, the stem 18 and adaptor assembly 16 can be inserted into the tibia 24, with the stem 18 being inserted into the first bore 110 such that the adaptor assembly 16 engages the second bore 112. Then, the mating portion 12 can be coupled to the adaptor assembly 16, as shown in FIG. 7. Generally, the bearing member 38 can be coupled to the first surface 56 of the tray 40 before the tray 40 is coupled to the adaptor assembly 16 (not specifically shown). Then, once the bearing member 38 is coupled to the tray 40, the sleeve 66 can be rotated as necessary within the adaptor 64 to properly align the tray 40, or to provide the best coverage of the tibia 24.

Once the offset bore 92 of the sleeve 66 is properly aligned, the bio-compatible cement B can be inserted into the bore 92 of the sleeve 66. Then, the mating projection 60 of the tray 40 can be inserted into the offset bore 92 of the sleeve 66. The insertion of the mating projection 60 into the offset bore 92 can cause the cement to flow around the grooves 62 of the mating projection 60 to assist in securing the tray 40 to the adaptor assembly 16 (as best shown in FIG. 2). Once the tray 40 is coupled to the adaptor assembly 16, the intercondylar recess 37 of the femoral component 8 can be mated with or coupled to the intermediate portion 50 of the bearing member 38 such that the first femoral bearing surface 34 and second femoral bearing surface 36 of the femoral component 8 are aligned with the first bearing portion 46 and the second bearing portion 48 of the bearing member 38.

Figure 8:
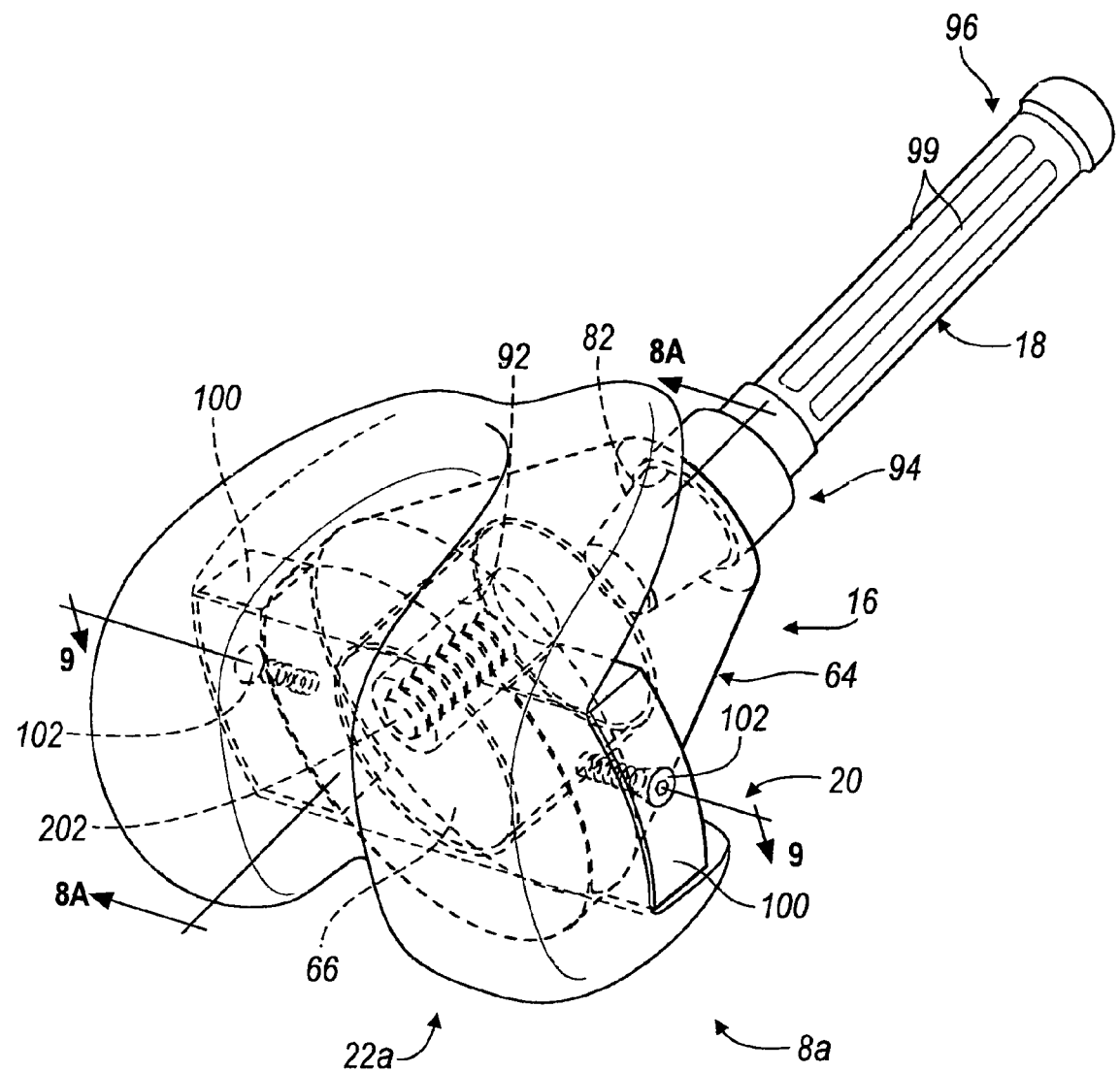
FIG. 8 is a perspective view of a third alternative knee implant according to the present disclosure.
Figure 8A:
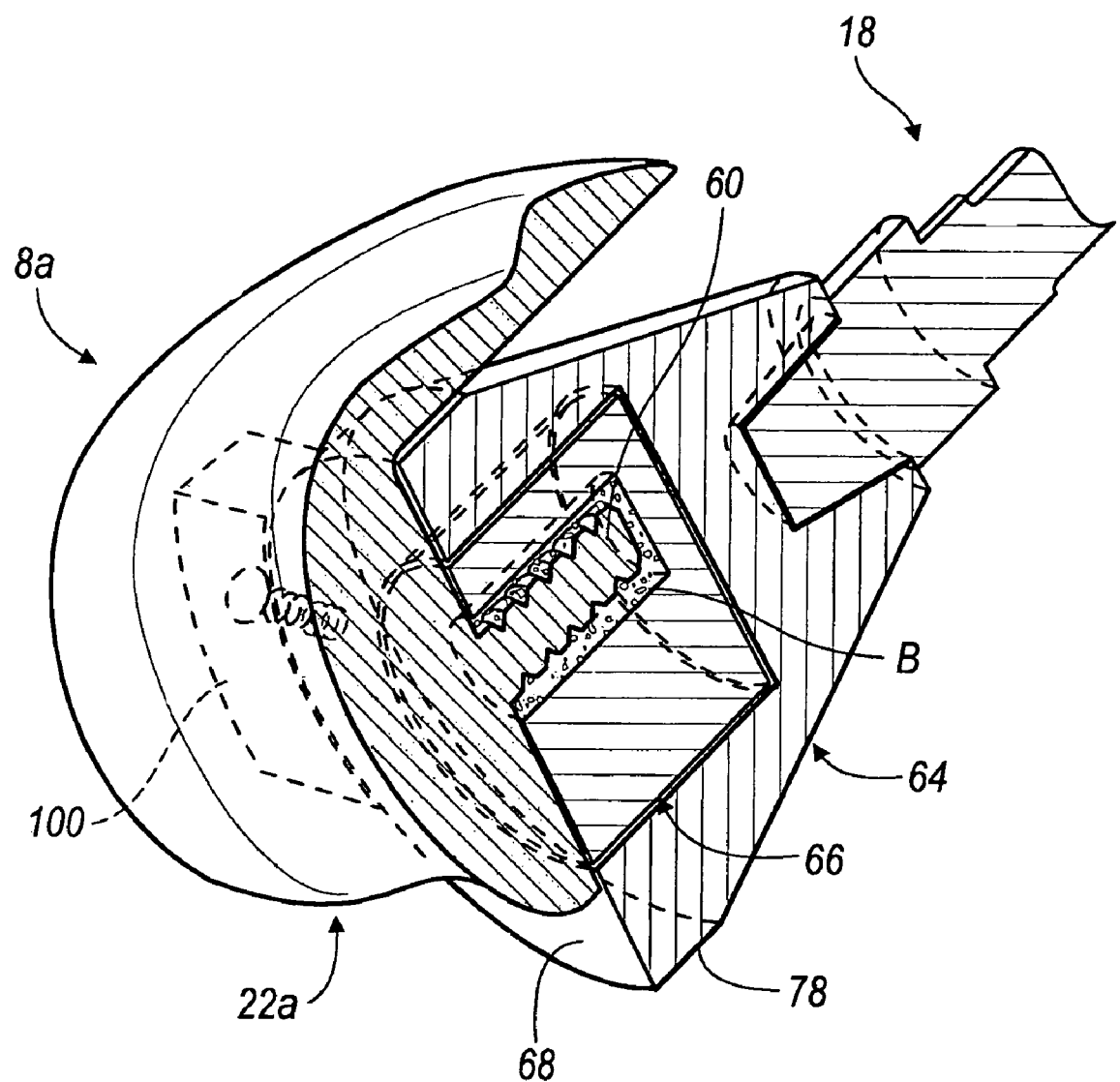
FIG. 8A is a cross-sectional view of the third alternative knee implant of FIG. 8, taken along line 8A-8A of FIG. 8.
Figure 9:
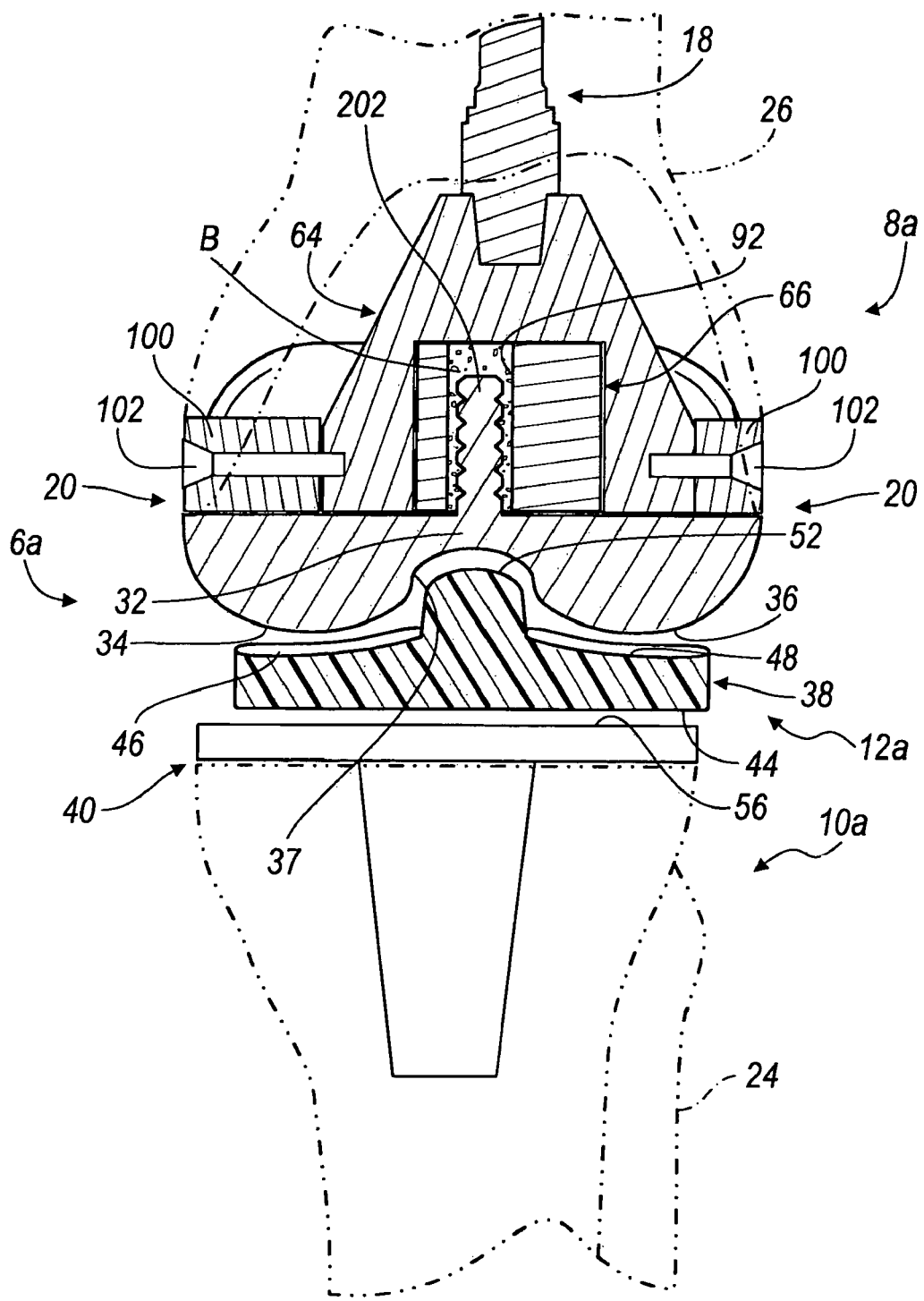
FIG. 9 is a cross-sectional view of the third alternative knee implant of FIG. 8, taken along line 9-9 of FIG. 8, illustrating the third alternative knee implant engaged with a selected portion of the anatomy.
Figure 10:
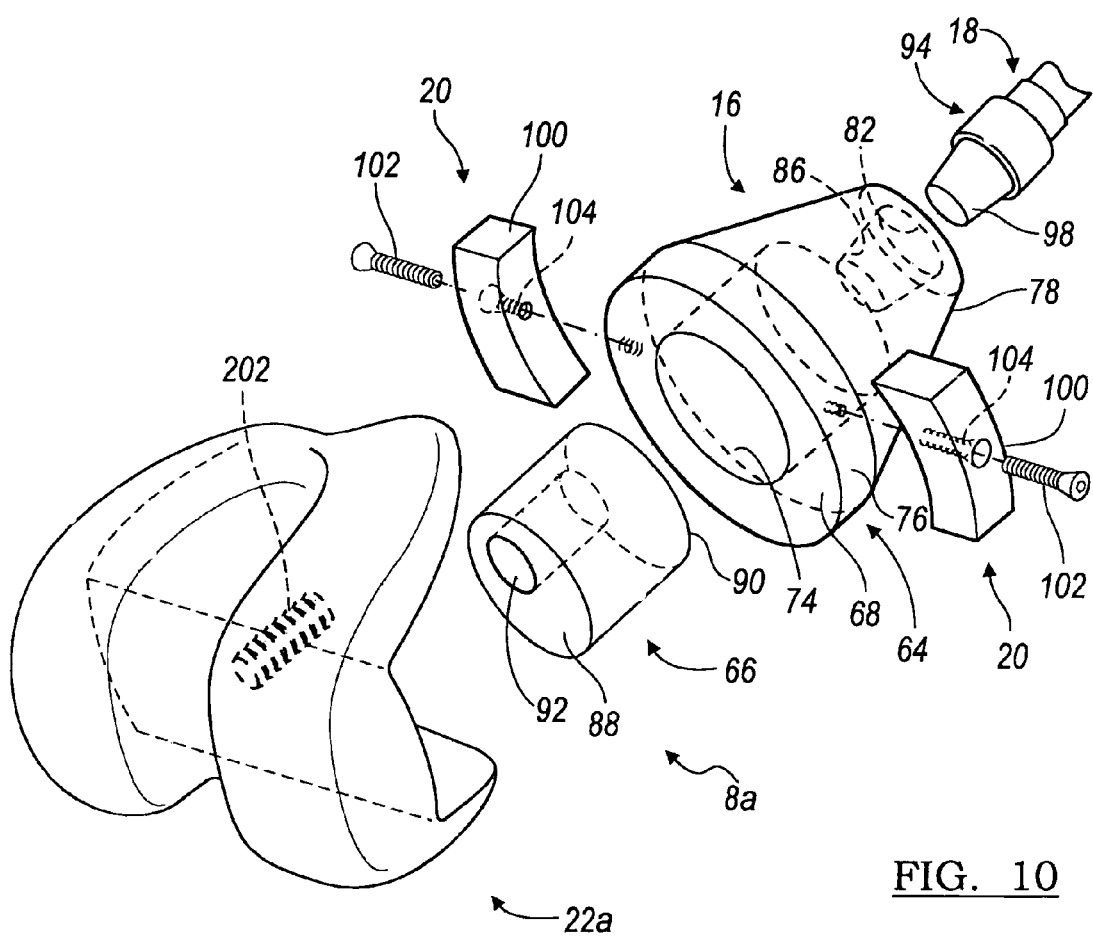
FIG. 10 is an environmental view of a first procedure for coupling the third alternative knee implant of FIG. 8 to the selected portion of the anatomy.
Figure 10A:
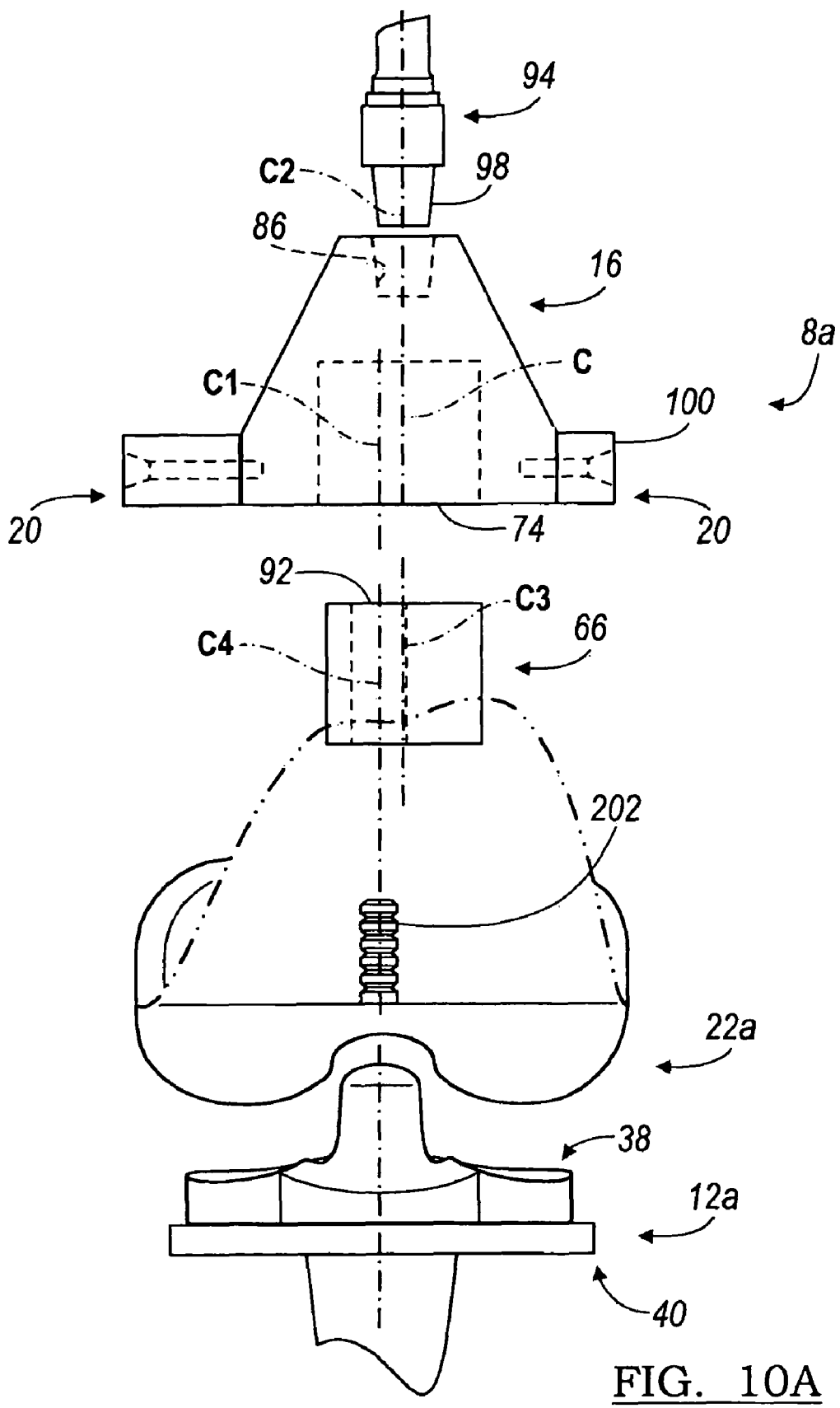
FIG. 10A is a front view of the knee implant of FIG. 10.

With reference now to FIGS. 8, 8A and 9, an alternative knee implant assembly 6a is shown. The alternative knee implant assembly 6a can include a femoral component 8a and a tibial component 10a. In the alternative knee implant assembly 6a, the adaptor assembly 16, stem 18 and augment system 20 can be coupled to the distal end of the femur 26 to form the femoral component 8a. The tibial component 10a can include an articulating or mating portion 12a to enable the femoral component 8a to articulate with respect to the tibial component 10a.

Figure 11:
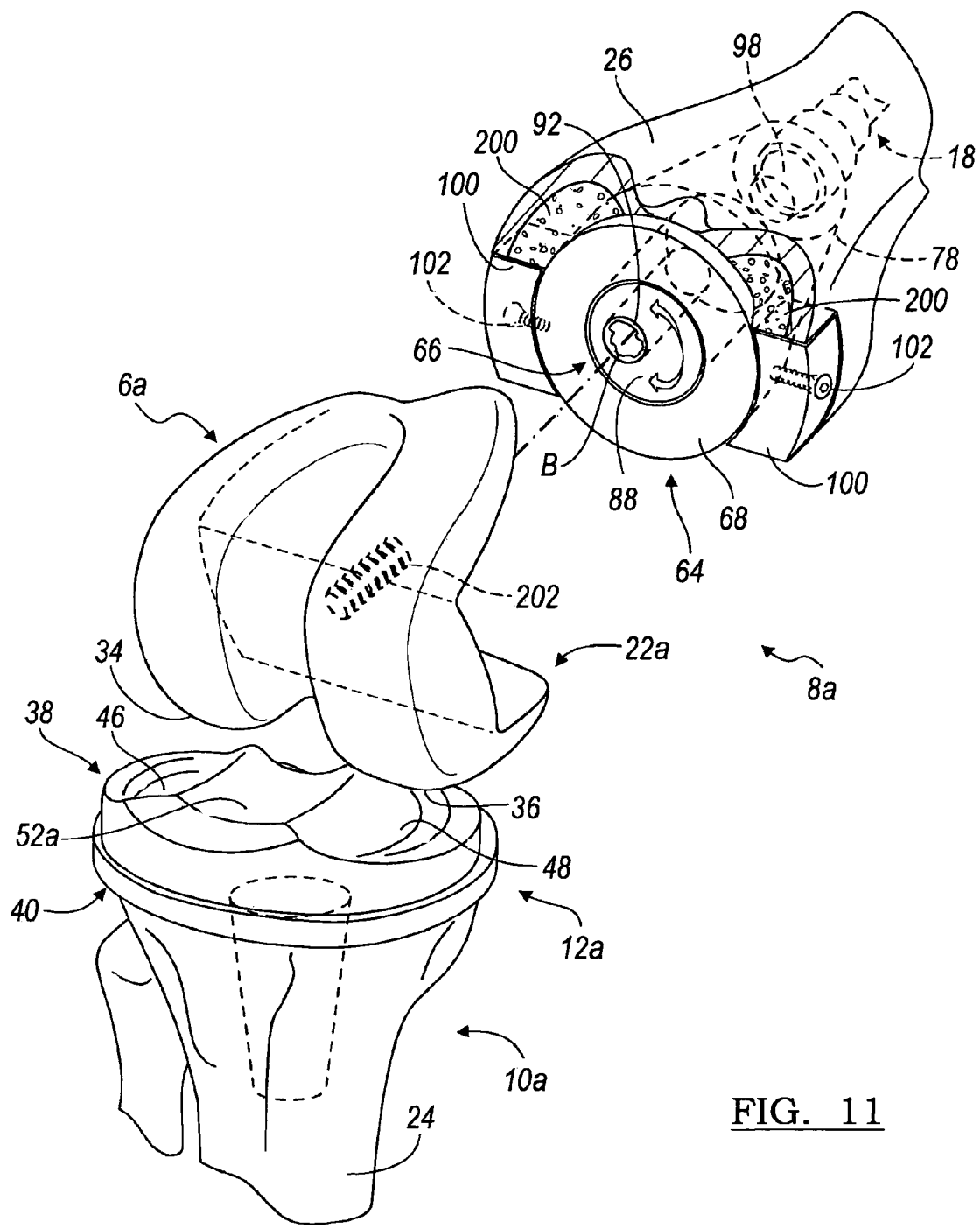
FIG. 11 is an environmental view of a second procedure for coupling the third alternative knee implant of FIG. 8 to the selected portion of the anatomy.

With continuing reference to FIG. 8, the femoral component 8a can include an articulating portion or body 22a, the adaptor assembly 16, the stem 18 and the augment system 20. As the adaptor assembly 16, stem 18 and augment system 20 are substantially similar to the adaptor assembly 16, stem 18 and augment system 20 described in conjunction with FIGS. 1-7, they will not be described in detail with regard to the femoral component 8a. It should be noted, however, that the augment system 20 of the femoral component 8a can generally include at least two augments 100, with at least one augment 100 per condylar surface 200 of the femur 26 (as best shown in FIG. 11).

With continued reference to FIGS. 8-10A, the body 22a of the femoral component 8a can include a post 202 coupled a surface 204 of the intercondylar portion 32 to couple the body 22a to the adaptor assembly 16. The post 202 can be configured to couple the femoral component 8a to the adaptor assembly 16. Generally, the post 202 can be sized to be received into the offset coupling axis or offset bore 92 of the sleeve 66. It will be understood that although the post 202 is shown as cylindrical, the post 202 can have any desired shape such as starred, oval, rectangular, square, or any other polygonal shape, and alternatively could be keyed to mate with the offset bore 92 of the sleeve 66.

The post 202 can include at least one or a plurality of grooves 206 to assist in coupling the post 202, and thus the body 22a, to the sleeve 66 of the adaptor assembly 16. The post 202 can be coupled to the bore 92 of the sleeve 66 through the use of a bio-compatible adhesive, such as the bio-compatible cement B. Alternatively, the body 22a could be coupled to the sleeve 66 via a bio-compatible mechanical fastener, such as a bolt or a screw, which could extend through a throughbore (not shown) in the body 22a to threadably engage threads (not shown) formed in the bore 92 of the sleeve 66.

The tibial component 10a, and the mating portion 12a of the alternative knee implant assembly 6a, can be any generally known suitable tibial component 10a and mating portion 12a, like the tibial component of the AGC® Total Knee System™, or the AGC® Tradition High-Post Knee System™, or the Orthopaedic Salvage System™, all provided by Biomet, Inc. of Warsaw, Ind. Alternatively, the tibial component 10a could be the tibial component 10 as described with reference to FIGS. 1-7.

With additional reference to FIG. 11, in order to couple the alternative knee implant assembly 6a to the anatomy, the tibia 24 and femur 26 (not shown) can be resected and prepared as is generally known in the art. In order to couple the femoral component 8a to the femur 26, the adaptor 64 can be coupled to the stem 18 and then the stem 18 can be press-fit into a first bore and a second bore formed in the femur 26 (not specifically shown). If the augment system 20 is employed, prior to insertion into the anatomy, the augments 100 and the most appropriate sleeve 66 can be coupled to the adaptor assembly 16, as discussed previously herein. Then, the sleeve 66 can be rotated until the offset bore 92 is in the desired orientation for mating the femoral component 8a with the tibial component 10a.

Once the sleeve 66 is properly aligned, the bio-compatible cement B can be placed into the offset bore 92 and then the post 202 of the body 22a can be inserted into the offset bore 92 to couple the body 22a to the adaptor assembly 16. After the body 22a is coupled to the adaptor assembly 16, the adaptor assembly 16 can be coupled to the stem 18, and then the stem 18 and adaptor assembly 16 can be inserted into the first bore and the second bore formed in the femur 26 (not specifically shown). Generally, when the adaptor 64 is coupled to the stem 18, the body 22a becomes properly engaged with the femur 26, and the tibial component 10a can then be coupled to the tibia 24, as is generally known in the art.

The description of the teachings herein is merely exemplary in nature and, thus, variations that do not depart from the gist of the teachings are intended to be within the scope of the teachings. Such variations are not to be regarded as a departure from the spirit and scope of the teachings.

What is claimed is:

1. A prosthesis for replacing an articulating portion of bone comprising:
   an adaptor defining a first cylindrical bore and positionable within the bone to replace a portion of the bone;
   an augment having an outer semi-circular sidewall removably coupled to a complementary portion of a cylindrical sidewall of the adaptor;
   a sleeve received substantially entirely within the first bore of the adaptor, the sleeve defining a second bore that has an offset coupling axis; and
   an articulating portion that replaces the articulating portion of the bone that includes a projection that is received within the second bore to couple the articulating portion to the adaptor;
   wherein the sleeve is positionable within the first bore of the adaptor to couple the articulating portion relative to the offset coupling axis of the second bore at a predetermined orientation and the second bore includes bone cement coupling the projection to the adaptor.

2. The prosthesis of claim 1, wherein the adaptor is composed of a porous metal material.

3. The prosthesis of claim 1, wherein the adaptor has a surface and an apex, and at least one tapered sidewall coupled between the cylindrical sidewall and the apex.

4. The prosthesis of claim 1, wherein the first bore is cylindrical and an outer surface of the sleeve is cylindrical to mate with the first bore.

5. The prosthesis of claim 4, wherein the sleeve is rotatably coupled to the first bore.

6. The prosthesis of claim 3, wherein the augment has an augment surface, the augment surface being coplanar with the adaptor surface when the augment is coupled to the portion of the cylindrical sidewall.

7. The prosthesis of claim 1, wherein the second bore is formed in the sleeve, offset from a central longitudinal axis of the sleeve.

8. The prosthesis of claim 3, wherein the adaptor further comprises a third bore defined in the apex.

9. The prosthesis of claim 8, further comprising:
   a stem having first end and a second end, the first end of the stem defining a coupling portion for mating with the third bore defined in the apex of the adaptor, the second end of the stem adapted to be coupled to a portion of the bone.

10. A prosthesis for replacing an articulating portion of bone comprising:
    a cylindrical sleeve extending along a central longitudinal axis and defining a first bore extending along an offset coupling axis;
    an adaptor positionable substantially entirely within the bone to replace a portion of the bone, the adaptor defining a second bore that receives the sleeve, the second bore having an inner cylindrical sidewall and an endwall, the sleeve fully positioned within the second bore such that the sleeve does not extend beyond the sidewall, the sleeve rotatable within the second bore, the adaptor having a surface and an apex, with at least one cylindrical sidewall adjacent to the surface and at least one tapered sidewall coupled between the at least one cylindrical sidewall and the apex, and the second bore is defined through the surface;
    an articulating portion operable to replace the articulating portion of the bone including a projection having a plurality of grooves, the projection received within the first bore to couple the articulating portion to the sleeve; and
    at least one augment, the at least one augment having an outer semi-circular sidewall removably coupled to a complementary portion of the at least one cylindrical sidewall of the adaptor and coupled to the adaptor with a fastener extending into the at least one cylindrical sidewall of the adaptor, and wherein the adaptor is composed of a porous metal material and a bone cement inserted into the first bore couples the projection of the articulating portion to the adaptor.

11. The prosthesis of claim 10, wherein the sleeve is rotatable to adjustably position the offset coupling axis to couple the articulating portion to the offset coupling axis at a predetermined orientation.

12. The prosthesis of claim 10, further comprising:
    a stem having first end and a second end, the first end of the stem defining a coupling portion, the second end of the stem adapted to be coupled to a portion of bone,
    wherein the apex of the adaptor defines an aperture for receipt of the coupling portion of the first end of the stem.

13. A prosthesis for replacing an articulating portion of bone comprising:
    a stem having first end and a second end, the first end of the stem defining a tapered coupling portion, the second end of the stem adapted to be coupled to a portion of bone,
    a cylindrical sleeve defining an offset coupling axis, the sleeve having a first terminal end and a second terminal end;
    a conical adaptor positionable within the bone to replace a portion of the bone, the adaptor including a substantially planar first surface, a substantially planar second surface opposite the first surface; an outer cylindrical sidewall adjacent to the first surface, an outer tapered sidewall extending from the cylindrical sidewall to the second surface, a first bore formed through the first surface, the first bore having an inner cylindrical sidewall and an endwall, with the sleeve positionable within the first bore such that the first terminal end is adjacent to the endwall of the first bore and the second terminal end is coplanar to the first surface, and a second tapered bore extending inward from the second surface and not communicating with the first bore, the second bore receiving the tapered coupling portion of the stem;
    an articulating portion operable to replace the articulating portion of the bone, the articulating portion coupled to the adaptor via the offset coupling axis; and
    a first augment having an outer semi-circular sidewall removably coupled to a complementary portion of the cylindrical sidewall of the adaptor, the first augment having a substantially planar augment surface, the augment surface being coplanar with the first surface of the adaptor when the first augment is coupled to the portion of the cylindrical sidewall, the first augment coupled to the adaptor with a fastener extending into the cylindrical sidewall of the adaptor.

14. The prosthesis of claim 13, wherein the sleeve is positionable within the first bore to couple the articulating portion to the offset coupling axis at a predetermined orientation.

15. The prosthesis of claim 13, further comprising:
a stem having first end and a second end, the first end of the stem defining a coupling portion, the second end of the stem adapted to be coupled to a portion of bone,
wherein the second surface of the adaptor defines an aperture for receipt of the coupling portion of the first end of the stem.

16. The prosthesis of claim 10, wherein the sleeve has a first terminal end and a second terminal end, the sleeve received within the second bore such that the first terminal end is adjacent to the endwall, and the second terminal end is coplanar to the surface.

17. The prosthesis of claim 3, wherein the adaptor is conical in shape.

18. The prosthesis of claim 1, wherein the projection includes a plurality of annular grooves.

19. The prosthesis of claim 10, wherein the at least one augment comprises first and second augments, wherein each of the first and second augments has an augment surface that is coplanar with the adaptor surface.

20. The prosthesis of claim 13, wherein the sleeve defines a second bore extending along the offset coupling axis and the articulating portion includes a projection having a plurality of grooves, the projection sized to be received within the second bore so that a bone cement inserted into the second bore couples the articulating portion to the adaptor.

21. The prosthesis of claim 10, further comprising a tibial tray coupled to the adaptor and having a planar surface extending beyond the cylindrical sidewall of the adaptor, and wherein the at least one augment has a planar augment surface mating with the surface of the tibial tray outside the adaptor.

22. The prosthesis of claim 10, further comprising a femoral component, the femoral component having an inner planar surface mating with a planar surface of the at least one augment.

23. The prosthesis of claim 22, wherein the at least one augment includes first and second augments of unequal sizes at opposite sides of the adaptor.

* * * * *